United States Patent
Pacheco

(10) Patent No.: US 12,186,030 B2
(45) Date of Patent: *Jan. 7, 2025

(54) INTRAOPERATIVE FLUOROSCOPIC REGISTRATION OF VERTEBRAL BODIES

(71) Applicant: Hector Pacheco, Encinitas, CA (US)

(72) Inventor: Hector Pacheco, Encinitas, CA (US)

(73) Assignee: LEUCADIA 6, LLC., El Paso, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/302,824

(22) Filed: Apr. 19, 2023

(65) Prior Publication Data

US 2023/0248448 A1 Aug. 10, 2023

Related U.S. Application Data

(63) Continuation of application No. 15/795,503, filed on Oct. 27, 2017, now Pat. No. 11,653,979.
(Continued)

(51) Int. Cl.
*A61B 34/20* (2016.01)
*A61B 6/00* (2024.01)
(Continued)

(52) U.S. Cl.
CPC ............ *A61B 34/20* (2016.02); *A61B 6/4441* (2013.01); *A61B 6/5235* (2013.01);
(Continued)

(58) Field of Classification Search
CPC . A61B 17/1703; A61B 17/1757; A61B 6/441; A61B 6/12; A61B 6/487;
(Continued)

(56) References Cited

U.S. PATENT DOCUMENTS 5,129,911 A * 7/1992 Siczek ................. A61B 6/502
378/162
5,291,537 A 3/1994 Mazess
(Continued)

FOREIGN PATENT DOCUMENTS

WO 2008/089429 7/2008

OTHER PUBLICATIONS

Extended European Search Report issued in EP Application No. 17865252.5 dated Sep. 18, 2020 (9 pages).
(Continued)

*Primary Examiner* — Marcela I. Shirsat
(74) *Attorney, Agent, or Firm* — Nixon & Vanderhye, P.C.

(57) ABSTRACT

A method for the fluoroscopic registration in real time for placement of pedicle screws or the like during spinal surgery, comprising creating a lateral image in which a pedicle has appropriate anatomic contour and superior endplate, advancing a pin into the pedicle starting in the posterior cortex and moved far enough into the pedicle to anchor the pin, rotating the fluoroscopy to obtain an AP image of the pedicle which is moved to render the pin to be neutral in a cephalad to caudad direction, and positioning a pedicle screw in the pedicle following 2D contour mapping generated by manual or automated templating.

12 Claims, 6 Drawing Sheets

Related U.S. Application Data

(60) Provisional application No. 62/413,579, filed on Oct. 27, 2016.

(51) Int. Cl.
 *A61B 6/12* (2006.01)
 *A61B 17/00* (2006.01)
 *A61B 17/16* (2006.01)
 *A61B 17/17* (2006.01)
 *A61B 90/00* (2016.01)
 *A61F 2/44* (2006.01)
 *A61F 2/46* (2006.01)

(52) U.S. Cl.
 CPC .......... *A61B 17/1757* (2013.01); *A61F 2/442* (2013.01); *A61F 2/4611* (2013.01); *A61B 6/12* (2013.01); *A61B 6/487* (2013.01); *A61B 2017/00907* (2013.01); *A61B 2017/0092* (2013.01); *A61B 17/1671* (2013.01); *A61B 17/1703* (2013.01); *A61B 2034/2065* (2016.02); *A61B 2090/067* (2016.02); *A61B 2090/0811* (2016.02); *A61B 2090/364* (2016.02); *A61B 2090/376* (2016.02); *A61F 2002/4635* (2013.01)

(58) Field of Classification Search
 CPC .................. A61B 6/5235; A61B 34/20; A61B 2034/2065; A61B 2090/0811; A61B 2090/376; A61B 2090/067; A61B 2090/364; A61F 2/4611; A61F 2/442; A61F 2002/4635
 USPC ............... 606/79; 623/17.11–17.16; 600/424
 See application file for complete search history.

(56) References Cited

U.S. PATENT DOCUMENTS

| | | | |
|---|---|---|---|
| 5,351,404 A | 10/1994 | Smith | |
| 5,575,798 A * | 11/1996 | Koutrouvelis | A61B 17/3403 606/130 |
| 5,591,207 A | 1/1997 | Coleman | |
| 5,682,886 A | 11/1997 | Delp | |
| 5,748,767 A | 5/1998 | Raab | |
| 5,772,594 A | 6/1998 | Barrick | |
| 5,799,055 A | 8/1998 | Peshkin | |
| 5,850,836 A | 12/1998 | Steiger | |
| 5,871,018 A | 2/1999 | Delp | |
| 6,002,959 A | 12/1999 | Steiger | |
| 6,048,331 A | 4/2000 | Tsugita et al. | |
| 6,069,932 A | 5/2000 | Peshkin | |
| 6,167,296 A | 12/2000 | Shahidi | |
| 6,175,758 B1 | 1/2001 | Kambin | |
| 6,198,794 B1 | 3/2001 | Peshkin | |
| 6,226,548 B1 | 5/2001 | Foley | |
| 6,282,437 B1 | 8/2001 | Franck et al. | |
| 6,351,662 B1 | 2/2002 | Franck et al. | |
| 6,470,207 B1 | 10/2002 | Simon et al. | |
| 6,477,400 B1 | 11/2002 | Barrick | |
| 6,484,044 B1 | 11/2002 | Lilienfeld-Toal | |
| 6,490,467 B1 | 12/2002 | Bucholz et al. | |
| 6,490,475 B1 | 12/2002 | Seeley et al. | |
| 6,529,765 B1 | 3/2003 | Franck et al. | |
| 6,546,277 B1 | 4/2003 | Franck et al. | |
| 6,697,664 B2 | 2/2004 | Kienzle III et al. | |
| 6,741,883 B2 | 5/2004 | Gildenberg | |
| 6,856,827 B2 | 2/2005 | Seeley et al. | |
| 6,978,166 B2 | 12/2005 | Foley et al. | |
| 7,107,091 B2 | 9/2006 | Jutras et al. | |
| 7,130,676 B2 | 10/2006 | Barrick | |
| 7,139,601 B2 | 11/2006 | Bucholz et al. | |
| 7,235,076 B2 | 6/2007 | Pacheco | |
| 7,278,970 B2 | 10/2007 | Goldenberg | |
| 7,396,360 B2 * | 7/2008 | Lieberman | A61B 17/1757 606/279 |
| 7,491,180 B2 | 2/2009 | Pacheco | |
| 7,623,902 B2 | 11/2009 | Pacheco | |
| 8,214,014 B2 | 7/2012 | Pacheco | |
| 9,119,572 B2 | 9/2015 | Gorek | |
| 11,653,979 B2 * | 5/2023 | Pacheco | A61B 17/1757 606/79 |
| 2002/0035321 A1 | 3/2002 | Bucholz et al. | |
| 2002/0038118 A1 | 3/2002 | Shoham | |
| 2002/0072686 A1 | 6/2002 | Hoey et al. | |
| 2002/0161368 A1 | 10/2002 | Foley et al. | |
| 2002/0183610 A1 | 12/2002 | Foley et al. | |
| 2003/0163040 A1 | 8/2003 | Gildenberg | |
| 2003/0187348 A1 | 10/2003 | Goodwin | |
| 2004/0019263 A1 | 1/2004 | Jutras et al. | |
| 2004/0044295 A1 | 3/2004 | Reinert | |
| 2004/0077939 A1 | 4/2004 | Graumann | |
| 2004/0092932 A1 | 5/2004 | Aubin et al. | |
| 2004/0092988 A1 | 5/2004 | Shaolian et al. | |
| 2004/0240715 A1 | 12/2004 | Wicket et al. | |
| 2005/0101970 A1 | 5/2005 | Rosenberg | |
| 2005/0171557 A1 | 8/2005 | Shoham | |
| 2005/0192575 A1 | 9/2005 | Pacheco | |
| 2005/0216026 A1 | 9/2005 | Culbert | |
| 2005/0228270 A1 | 10/2005 | Lloyd et al. | |
| 2005/0251026 A1 | 11/2005 | Stone | |
| 2005/0267354 A1 | 12/2005 | Marquart et al. | |
| 2006/0025668 A1 | 2/2006 | Peterson et al. | |
| 2006/0058616 A1 | 3/2006 | Marquart et al. | |
| 2007/0016199 A1 * | 1/2007 | Boehm | A61B 17/1757 606/279 |
| 2007/0219554 A1 * | 9/2007 | Landry | A61B 17/7035 623/17.16 |
| 2009/0138053 A1 | 5/2009 | Assell | |
| 2010/0198271 A1 | 8/2010 | Leone | |
| 2014/0128979 A1 | 5/2014 | Womble | |
| 2018/0116733 A1 | 5/2018 | Pacheco | |

OTHER PUBLICATIONS

International Preliminary Report on Patentability dated May 3, 2019, issued in Application No. PCT/US2017/058689 (14 pages).
International Search Report and Written Opinion dated Jan. 26, 2018 issued in PCT/US2017/058689 (13 pages).
Toshitaka Yoshii, et al., "Lumbosacral pedicle screw placement using a fluoroscopic pedicle axis view and a cannulated tapping device" Journal of Orthopaedic Surgery and Research May 28, 2015, 10:79 [online], [retrieved on Dec. 13, 2017]. Retrieved from https://www.ncbi.nim.nih.govipmdarticiesiPMC4450.

* cited by examiner

INTRAOPERATIVE FLUOROSCOPIC REGISTRATION OF VERTEBRAL BODIES

CROSS-REFERENCES TO RELATED APPLICATIONS

This application is a continuation application of U.S. application Ser. No. 15/795,503, which claims the benefit of U.S. Provisional Patent Application No. 62/413,579 filed on Oct. 27, 2016. The entire contents of each of which are hereby incorporated by reference in their entireties.

FIELD OF THE INVENTION

The present invention relates to the general field of spinal surgery and, more particularly, to the enhancement of fluoroscopic registration in real time for placement of pedicle screws, vertebral augmentation or interbody spacers/artificial discs during spine surgery.

BACKGROUND OF THE INVENTION

Placement of screws into the human spine is a common surgical procedure to allow for a multitude of spinal surgeries to be performed. Screws are typically placed into the pedicles of individual vertebra in the lumbar and sacral spine. Given their biomechanical advantages over other modes of fixation, surgeons are expanding the areas of the spine in which pedicle screws are placed. However, adjacent to the spine are numerous vital structures and organs, in particular the cervical and thoracic spine regions, which have very low tolerance for surgically created injuries that may ultimately lead to significant morbidity and/or mortality. For this reason the majority of research focus on placement of pedicle screws is centered on improving accuracy to maintain a screw within a bony (intraosseous) environment.

Image guided systems are evolving which are increasingly user friendly to assist a surgeon in accurately placing a screw. The critical parameters for placing a pedicle screw into the human spine are diameter, length, trajectory and then actual placement of the screw. To date many of the image guidance systems allow for manual determination of these parameters to improve a surgeon's manual performance in screw placement. Up to the present time, no system is available which will automatically determine ideal pedicle screw diameter, length and trajectory for accurate placement of pedicle screws. The present invention provides this capability akin to a pilot who flies an airplane with computer controlled aviation capabilities, and allows for placement of pedicle screws using either an open or percutaneous technique.

Patent Application Publication No. U.S. 2004/0240715 A1, published on Dec. 2, 2004, relates to methods and computer systems for determining the placement of pedicle screws in spinal surgery. It discloses a method wherein the minimum pedicle diameter is first established for determining the optimum screw trajectory and then the maximum screw diameter and length using the optimum trajectory for each pedicle. Two dimensional transverse slice data is stacked to form three dimensional data points to determine optimum trajectory by linear least squares solution to fit the data, requiring the solution to go through the overall minimum transverse pedicle widths. A disadvantage of this method is that it allows for eccentric trajectory determination, particularly for distorted pedicle anatomy, with consequent smaller maximum diameter and length screw determinations resulting in biomechanically inferior constructions.

A new and improved method disclosed in U.S. Pat. No. 7,235,076 always places the trajectory concentrically through the pedicle by the determination of optimum trajectory by using the center point of the smallest cross sectional area (isthmus) and projecting with a computer a line normal to this circumscribed area in opposite directions. This new and improved method allows for maximum screw diameter and length determinations for intraosseous placement.

SUMMARY OF THE INVENTION

The present invention is an improvement of the method disclosed in U.S. Pat. No. 7,235,076. To enhance the fluoroscopic registration in real time for placement of pedicle screws, vertebral augmentation or interbody spacers/artificial discs during spine surgery a lateral image is taken in which the pedicle has appropriate anatomic contour and superior endplate is adequately visualized. Once this image is obtained then a pin, smooth or threaded, is advanced with a drill or otherwise starting in the posterior cortex and advanced far enough into the vertebral body until adequate bony purchase is obtained to hold it firmly anchored. This is particularly effective for regions with significant deformity or in the lumbosacral junction to identify the sacrum. Once this is achieved then the fluoroscopy or similar imaging is rotated to obtain an AP image for each individual vertebral body and angled, rotated or moved to obtain an AP image which renders the pin which was placed in lateral imaging to be neutral in a cephalad to caudad direction, and in congruence with 2D contour mapping generated by U.S. Pat. No. 7,235,076. Placement of pedicle screws, vertebral augmentation or interbody spacers/artificial discs in or adjacent to the pedicle then follows the 2D contour mapping generated by manual templating or integrated with automated templating generated by appropriate software.

By utilizing pins placed into the spine a targeting device can be connected to them such that it allows for placement of a cannula, awl or variable adjustable awl with built-in goniotometer/level to advance into pedicle for screw, cement or assisting with interbody device placement. This targeting device can be placed on patient's skin for minimally invasive surgery (MIS) or open surgery placement.

BRIEF DESCRIPTION OF THE DRAWINGS

FIG. 8b is a perspective view of a display for the awl shown in FIG. 8a;

DETAILED DESCRIPTION OF THE INVENTION

Figure 1:
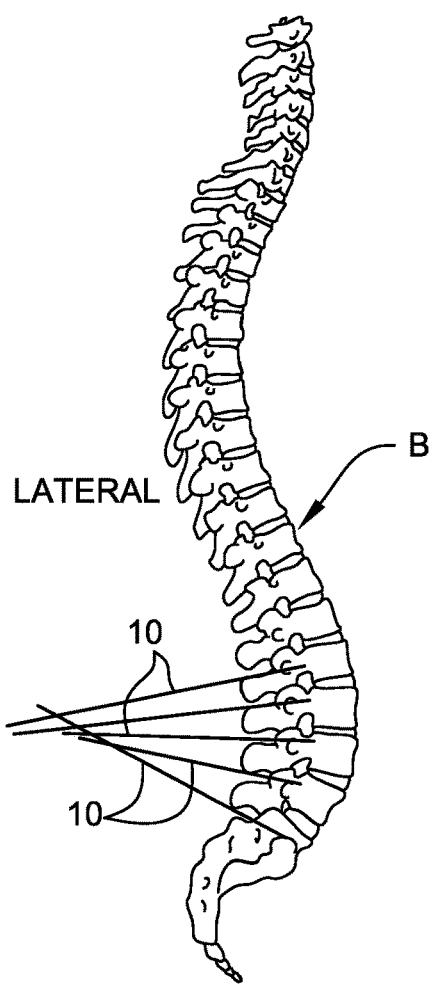
FIG. 1 is a lateral computer image of a bony spine in which one or more pins are inserted using lateral fluoroscopy into the posterior cortex of vertebral body and/or pedicles starting in the posterior cortex.
Figure 3:
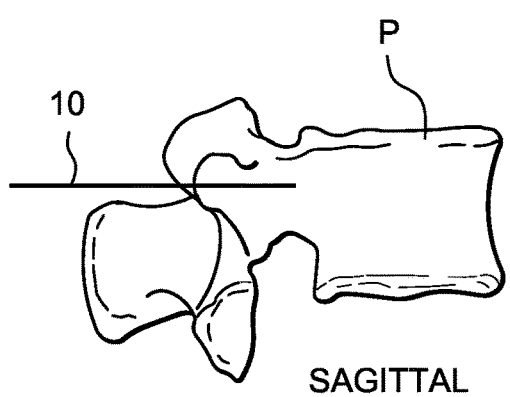
FIG. 3 is a computer image of a pin inserted in a posterior cortex in the lateral sagittal view of FIG. 1.

To enhance the fluoroscopic registration in real time for placement of pedicle screws, vertebral augmentation or interbody spacers/artificial discs during spine surgery, a lateral image is taken by a computer or other device in which the pedicle P has appropriate anatronic contour and superior end plate is adequately visualized. Once this image is obtained, a pin 10, smooth or threaded, formed of any suitable material is advanced with a drill or other device starting in the posterior cortex and advanced far enough into the vertebral body B until adequate bony purchase is obtained to hold it firmly anchored, as shown in FIGS. 1 and 3. This is particularly effective for positioning pedicle screws or other devices in regions with significant deformity or in the lumbosacral junction to identify the sacrum.

Figure 2:
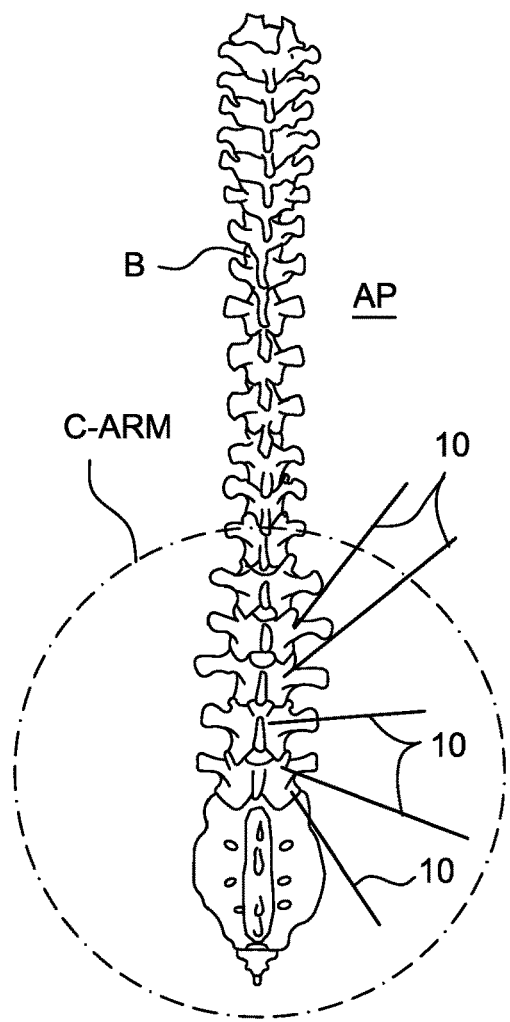
FIG. 2 is a computer image in which the fluoroscopy or similar imaging of FIG. 1 is rotated to obtain an AP image for each vertebral body and angled, rotated or moved to obtain an image which renders the pins placed in lateral imaging to be neutral in a cephalad to caudad direction and congruent with 2D contour mapping from U.S. Pat. No. 7,235,076.
Figure 4:
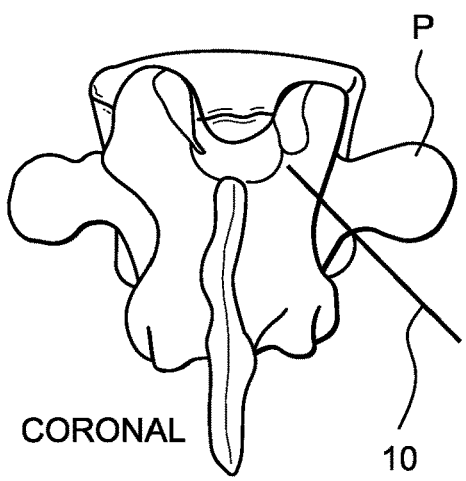
FIG. 4 is a computer image of a pin inserted in a pedicle in the AP coronal view of FIG. 2.

Once this is achieved, the fluoroscopy or similar imaging is rotated to obtain an AP image for each individual vertebral body B and angled, rotated or moved to obtain an AP image which renders the pin 10 placed in lateral imaging to be neutral in a cephalad to caudad direction, as shown in FIGS. 2 and 4. Placement of pedicle screws, vertebral augmentation or interbody spacers/artificial discs in or adjacent to the pedicle then follows the 2d contour mapping generated by manual templating or integrated with automated templating generated by appropriate software. The pin or pins 10 facilitate the placement of pedicle screws or other devices.

Figure 5:
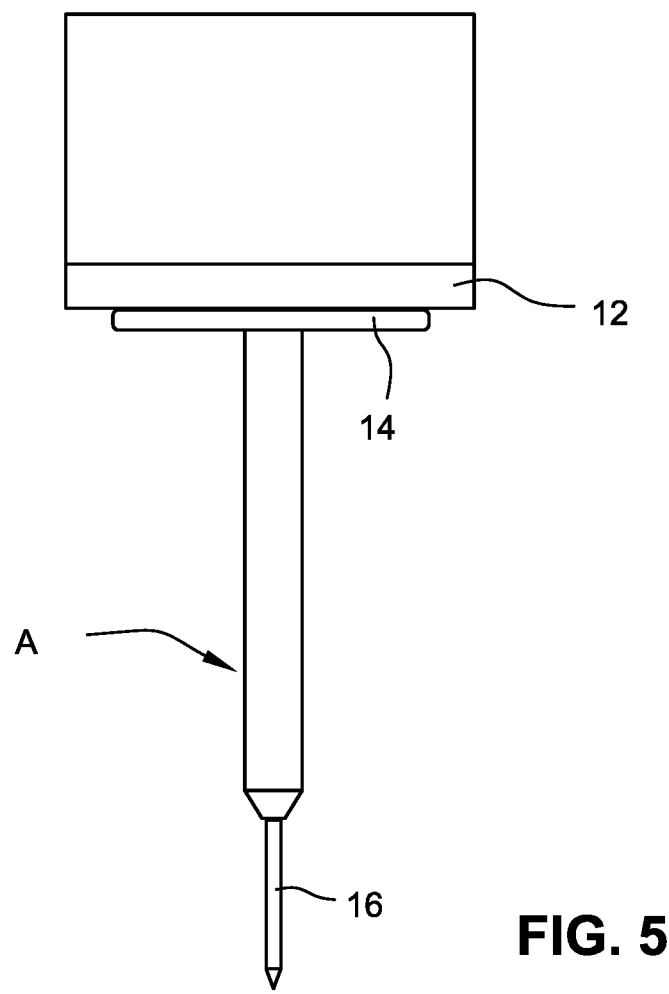
FIG. 5 is a side elevational view of an awl attached to a C-arm housing.
Figure 6:
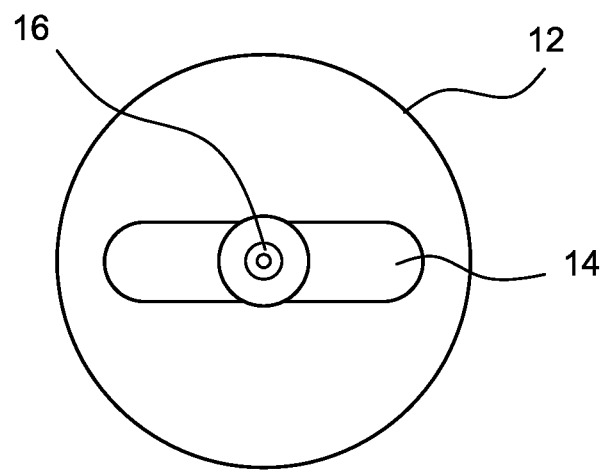
FIG. 6 is a bottom plan view of the awl shown in FIG. 5.

FIGS. 5 and 6 illustrate an awl A which is constructed to be attached to a C-arm housing 12 that enables the coupling of the awl A to a C-DRM. The awl A is provided with a handle 14 and a tip 16.

Figure 7:
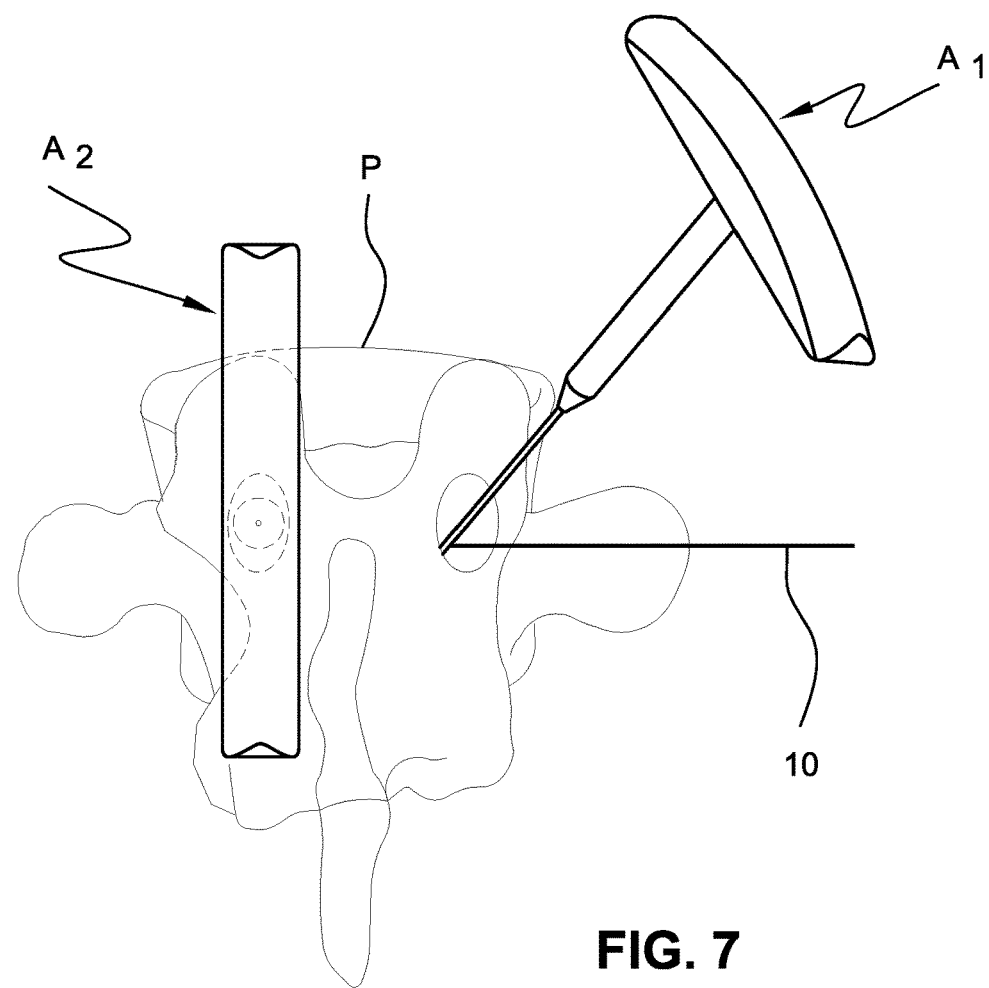
FIG. 7 is a coronal view of a vertebral body showing an awl not zeroed out and an adjacent pin, and an awl zeroed out.

FIG. 7 illustrates manual registration of an awl A with a C-arm to obtain zero degree coordinates after vertebral body B registration and a laterally placed pin 10. The awl A, is not zeroed out and is adjacent to the pin 10. The awl $A_2$ is zeroed out.

Figure 8A:
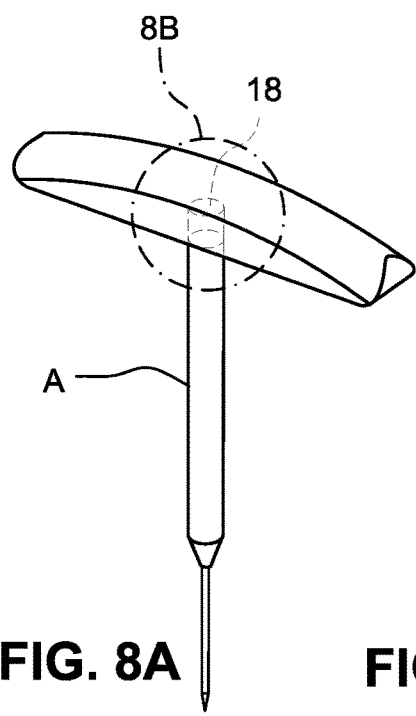
FIG. 8a is a perspective view of an awl with a built in goniometer to obtain coronal, sagittal and transverse registration using a digital or visual output display.
Figure 8B:
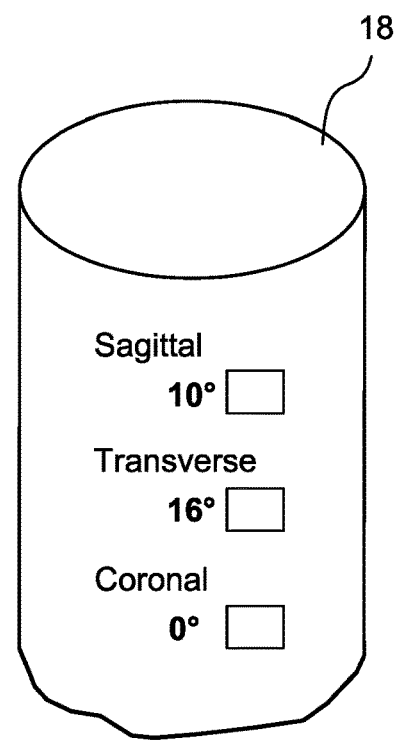

FIGS. 8a and 8b illustrate an awl A with a built in goniometer 18 to obtain coronal, sagittal and transverse registration with appropriate software using digital or visual output display.

Figure 9:
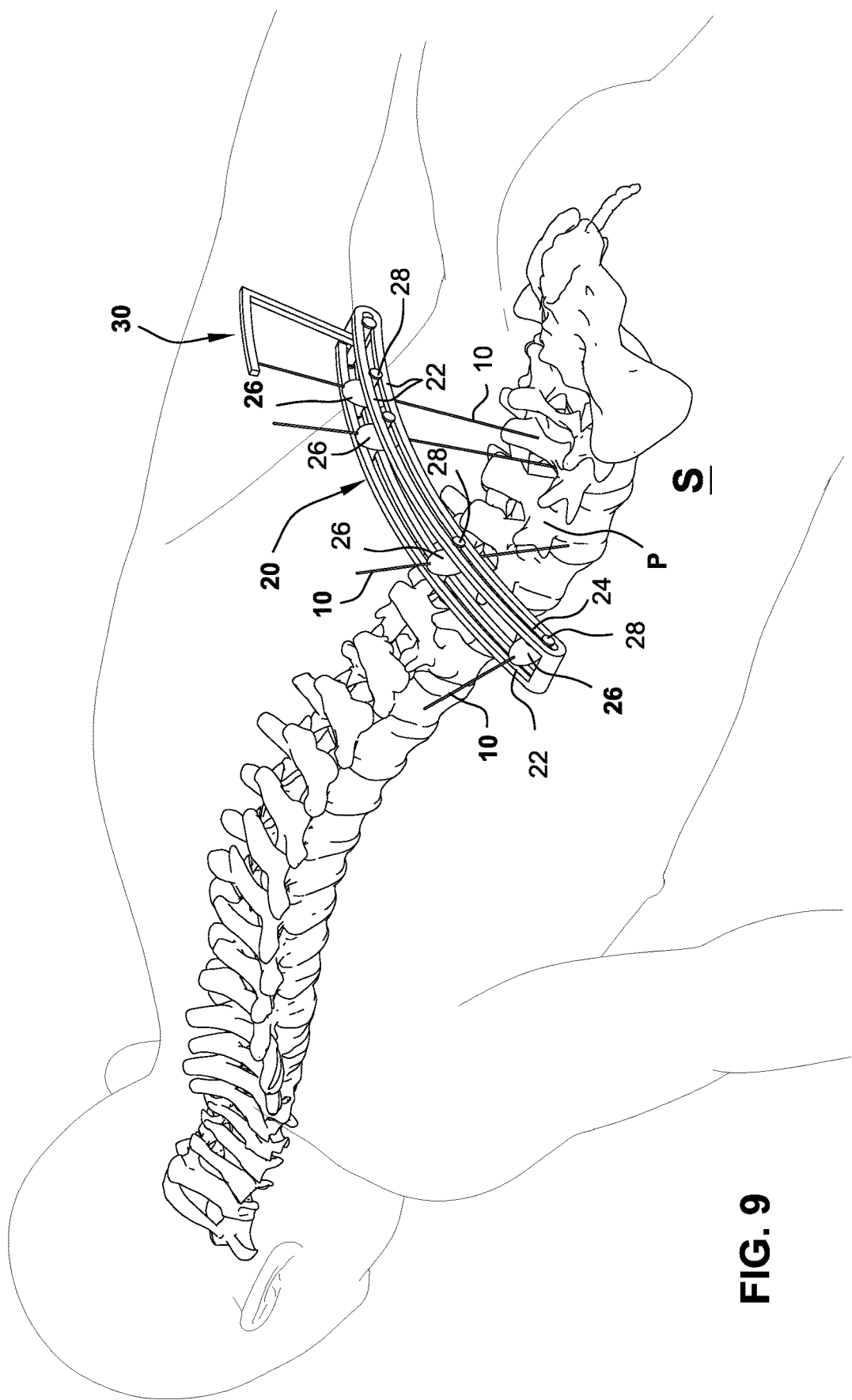
FIG. 9 is a perspective of a targeting device mounted on a patient's back for guiding pins to be positioned in the spine.
Figure 10:
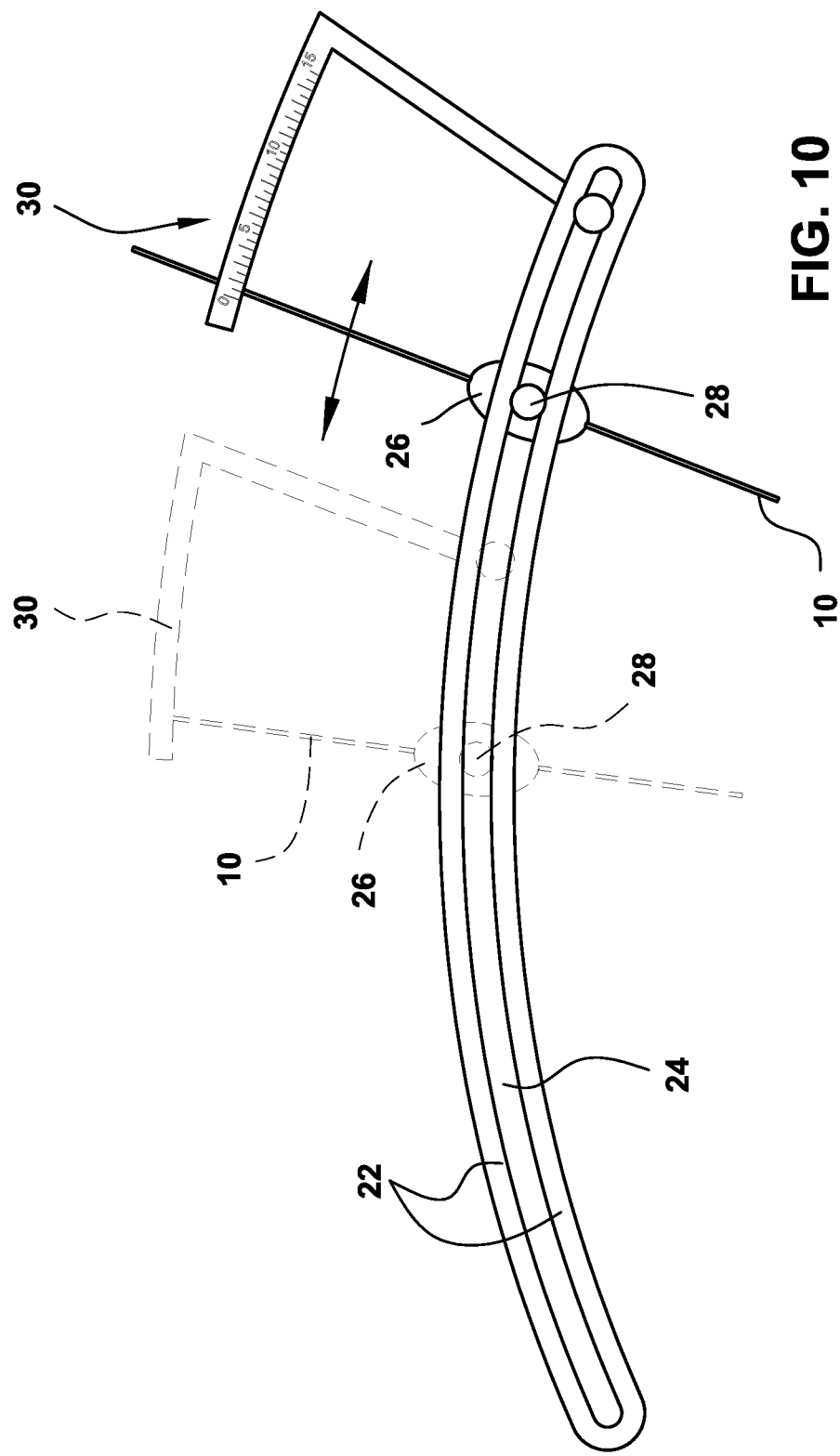
FIG. 10 is a partial side elevational view of the targeting device shown in FIG. 9.
Figure 11:
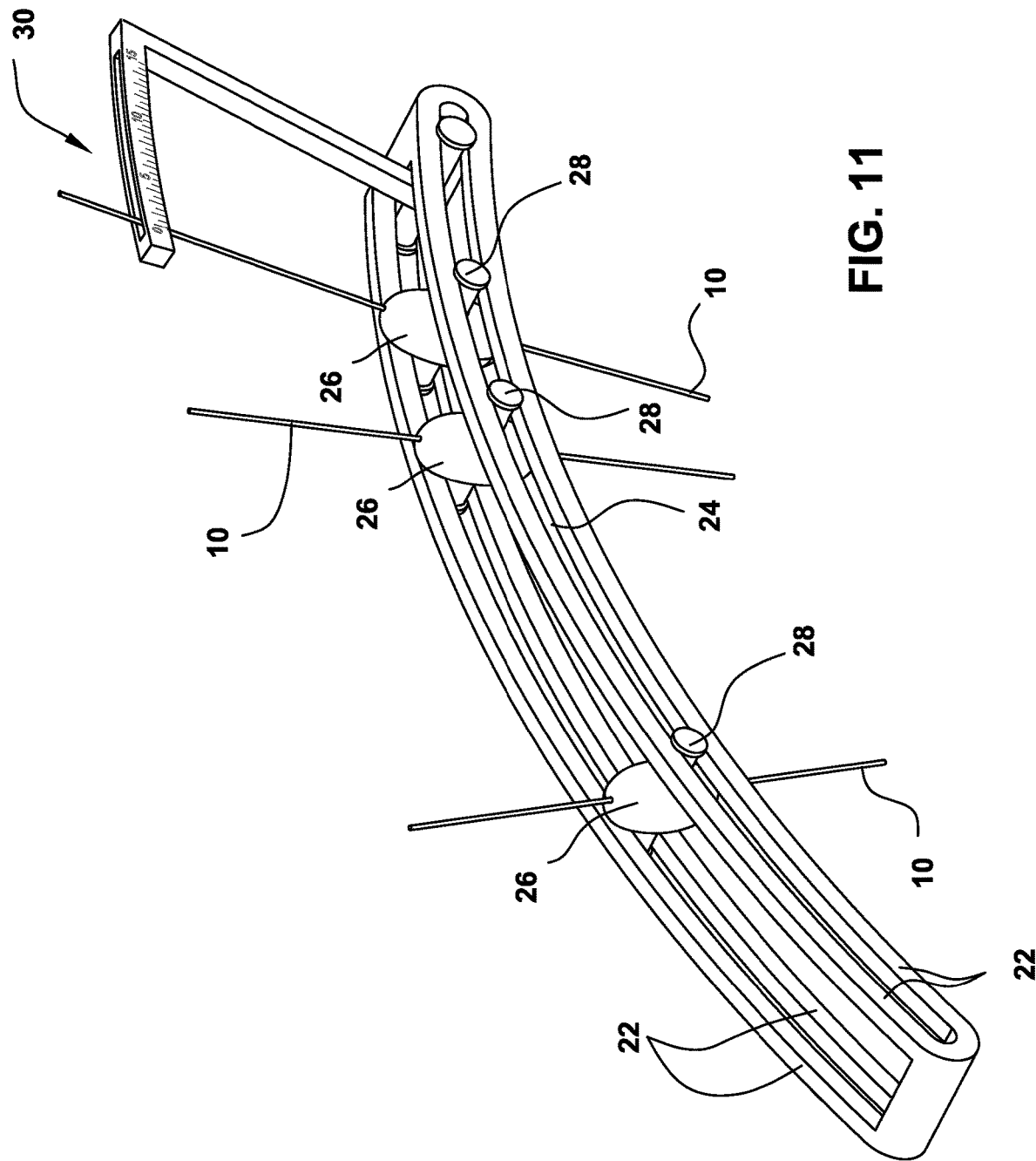
FIG. 11 is a partial perspective view of the adjusting mechanism of the targeting device.

A targeting device is illustrated in FIGS. 9-11 wherein, by utilizing pins 10 placed into the spine S, the targeting device T can be connected to them such that it allows for placement of, for example, cannula, and different types of awls to advance into the pedicle for screw, cement or assisting with interbody placement. The targeting device can be placed on a patients' skin for minimally invasive surgery or open surgery placement.

The targeting device comprises a housing 20 that may be radiolucent and is provided with spaced rails 22 defining a track 24 in which pin guides 26 are slidably mounted on ball bearings 28 or the like. Pins 10 are slidably mounted in the guides 26 and one or more angled guide devices 30 are operatively connected to the guides 26 and pins 10 to move them to desired positions on the patient.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A method for enhancement of fluoroscopic registration in real time for placement of pedicle screws, vertebral augmentation or interbody spacers/artificial discs during spine surgery, comprising:
    creating, by an imaging device in a first position for lateral imaging, a lateral image of a vertebral body in which a superior endplate is at least partially visualized,
    rotating the imaging device from the first position to a second position for Anterior-Posterior (AP) imaging to obtain an AP image of a pedicle, wherein the obtained AP image matches a 2D contour mapping generated by manual templating or automated templating, and
    positioning a pedicle screw, vertebral augmentation, interbody spacer, or artificial disc in or adjacent to the pedicle following the 2D contour mapping.

2. The method of claim 1 wherein a targeting device comprising a housing is provided for the placement of an awl into pedicles for screw, cement or interbody device placement.

3. The method of claim 2 wherein the targeting device is adapted to be placed on a patient's skin for minimally invasive surgery or open surgery placement.

4. The method of claim 2 wherein multiple pins is connected to the housing to provide for the placement of the awl into the pedicles for screw, cement or interbody device placement.

5. The method of claim 4 wherein the multiple pins are movably mounted within pin guides that are slidably mounted on a track of the targeting device.

6. The method of claim 5 wherein the track is curved so that the position and angle of the multiple pins can be adjusted.

7. The method of claim 6 wherein the multiple pins and the pin guides are operatively connected to one or more angled guide devices for moving them to desired positions on a patient.

8. The method of claim 6 wherein the housing of the targeting device is radiolucent.

9. The method of claim 2 wherein the awl is provided with a goniometer.

10. The method of claim 2 wherein the awl is attached to a C-arm housing and removably detachable.

11. The method of claim 1 wherein a targeting device comprising a housing is connected to multiple pins to provide for the placement of a cannula into pedicles for screw, cement or interbody device placement.

12. The method of claim 1 wherein the imaging device is rotated from the first position to the second position for Anterior-Posterior (AP) imaging after the creation of the lateral image of the vertebral body in which the superior endplate is at least partially visualized.

* * * * *